United States Patent [19]

Simhoni

[11] 4,409,975
[45] Oct. 18, 1983

[54] NEGATIVE HEEL PROTECTOR CUSHION

[76] Inventor: Orit Simhoni, P.O. Box 640134, Miami, Fla. 33164

[21] Appl. No.: 268,348

[22] Filed: May 29, 1981

[51] Int. Cl.³ .............................................. A61B 19/00
[52] U.S. Cl. ................................................... 128/153
[58] Field of Search .................... 128/153, 149, 132 R, 128/80 R

[56] References Cited

U.S. PATENT DOCUMENTS

| | | | |
|---|---|---|---|
| 3,693,619 | 9/1972 | Williams | 128/153 |
| 4,186,738 | 2/1980 | Schleicher et al. | 128/153 |
| 4,278,079 | 7/1981 | Simhoni et al. | 128/153 |

Primary Examiner—John D. Yasko
Attorney, Agent, or Firm—Eugene F. Malin

[57] ABSTRACT

A therapeutic support device to prevent decubitus ulceration on the heel of the foot or to assist in the healing of a decubitus ulcer on the heel area comprising a resilient foot supporting body having a plurality of resilient, separable layers joined together in a stacked array by a pair of straps which can be adjusted in size and arranged crossed or in parallel for an individual foot, the straps holding the layers together and the support body to the foot itself. Each individual layer includes a central aperture such that the stacked array has a heel receiving central chamber. The top layer includes a cut out portion for receiving the Achilles' tendon area of the patient. The device supports the foot of a supine or side-lying patient, while allowing the skin area of the heel to be free from contact with the bed or any surrounding surface. The number of layers may be selected to adequately support a particular weight foot; the upper layer may be replaced periodically for hygenic purposes. The top surface of the middle layer has a pocketed contour for improving pressure distribution and comfort of the patient. The holding straps that engage the foot may also be padded. The bottom surface of the bottom layer is pocketed for decreasing surface contact to generate a patient sensation of light weight. The peripheral lateral walls are concave to accommodate the shape of the foot in a side layer position.

2 Claims, 5 Drawing Figures

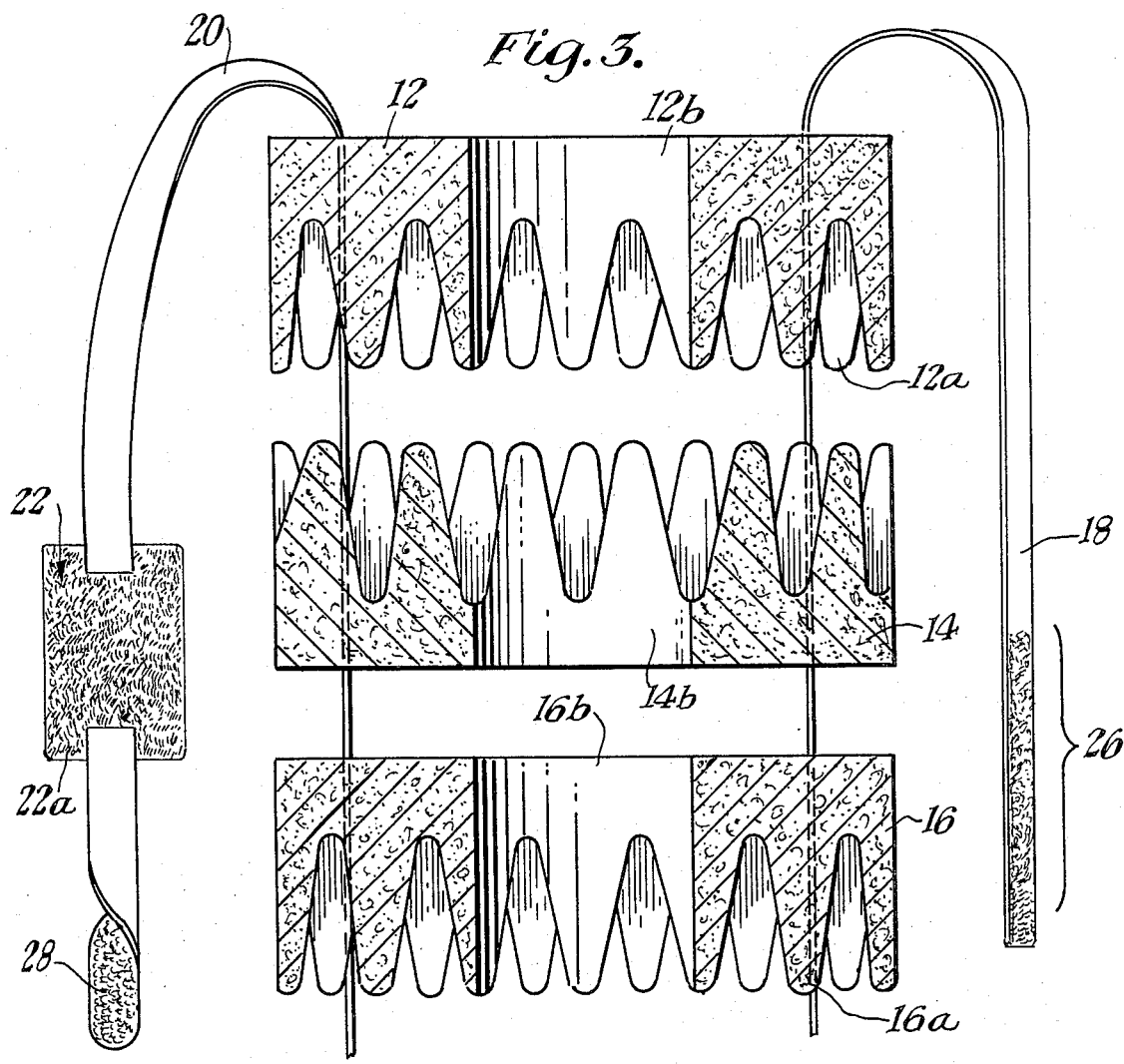
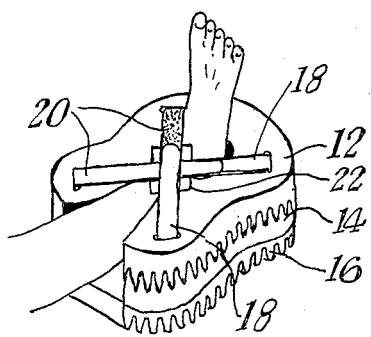
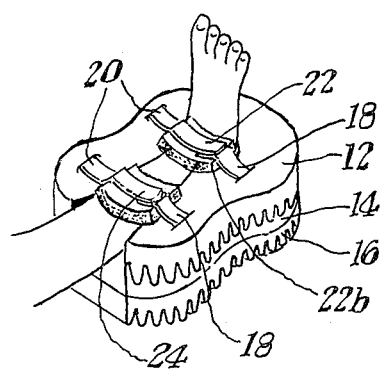

NEGATIVE HEEL PROTECTOR CUSHION

BACKGROUND OF THE INVENTION

This invention relates generally to a device for use in enterostimal therapy, which deals with the prevention or treatment of bedsores. Bedsores are commonly formed due to nonuniform pressure on the skin areas of patients who must spend long periods of time in bed. The main treatment of bedsores is to provide pressure relief, especially in those areas of the body where greater pressures are normally experienced by the patient. Because of the shape and structure of the human body and the foot, bedsores on the heel area of the foot are common among some hospital patients, such as diabetics who have circulation problems and patients with paralysis or skin problems.

The prior art discloses devices used as orthopedic supports, such as abduction pillows. Such a device is shown in U.S. Pat. No. 4,135,504. In that device, the feet are supported on a single layer to prevent foot droop. A foot protector is shown in U.S. Pat. No. 3,511,233. The holding straps and surface contact detract from the operation of the device.

The present invention is directed specifically for the treatment or prevention of bedsores and provides an improved foot support which is not limited to orthopedic patients, but is useful for the treatment of any patient that might experience bedsores. The present invention allows a patient's heels to remain off and out of contact with the bed surface, whether in a prone, supine, or side-lying position. The present invention also allows for the expeditous application of medicants for the heel area (such as stomaseal) by the therapist. With the present invention, it also enables the patient to exercise dorsi-flexion or plantar-flexion and inversion and eversion at the ankle and flexion or extension at the knee or hip, because of the lightweight and noncumbersome structure of the present invention. Additional advantages of the present invention are the non-complex adjustment to accommodate different weights for different patients to insure enough layers for proper vertical support above the bed, without making the device exceedingly cumbersome on the foot; removable layers for periodic replacement due to hygenic considerations; and reduced pressure on the dorsal portion of the foot because of the crossed strap or parallel foot connections. The present invention enhances dorse flexion and reduces patient skin contact.

BRIEF DESCRIPTION OF THE INVENTION

A device for supporting a human foot of a prone, supine, or side-lying patient for suspending the heel area free of support contact to prevent or treat decubitus ulceration on the heel. The device includes a plurality of resilient foam layers, each approximately one to two inches in height (or thickness) and preferably made from a product known under the trademark ZIMFOAM, the layers being joined together in a stacked, vertical array by a pair of web-like straps connected through each layer and issuing from the top of the device, the straps being a sufficient length for engagement around the dorsal area of the patient's foot.

The straps further include fabric-like fasteners, known under the trademark VELCRO, or vel foam disposed near each free end for the length of each strap to fit the device to a particular foot. The straps are fastened together and threaded through in a layer aperture to form either a criss-cross pattern over the top of the foot or a parallel pattern, as desired to change pressure position of the straps themselves.

Each individual foam layer includes a centrally located aperture which when joined together with other layer apertures coaxially forms a central heel receiving chamber disposed through the entire thickness or height of the supporting device. Each layer may be quickly removed or installed on the straps for enlargement or reduction in the overall thickness of the support for variations necessitated by differences in weight or sizes of the patient's foot.

The top layer has a cut out segment to receive the calf and Achilles' tendon of the patient to enhance dorsiflexion in the support position.

The middle supports the leg in the supine position and includes an upper concave surface to reduce contact pressure. The bottom surface of the top layer is also convoluted for improved holding contact with the middle layer.

The middle layer that contacts the patient's foot may be removed and replaced when necessary for hygenic and cleanliness purposes.

The peripheral shape of the device has lateral concave areas to accommodate the patient's foot or positioning of the patient's foot, either in a supine or side lying position. The concave areas reduce foot contact in the side lying position and total weight of the support.

The central aperture in each layer and therefore, in the entire heel supporting chamber, is sized to contact the foot in such a way that the heel area is free from any contact, either with the support itself or the bed surface. The aperture of the top layer and middle layer may be individually cut to fit a particular patient's foot to insure noncontact of the heel area when placed within the central chamber.

It is an object of this invention to provide a foot supporting device that is noncomplex in construction and is useful for the treatment or prevention of bedsores on the heel area of a prone, supine, or side-lying patient.

It is another object of this invention to provide an enterostimal therapeutic device which may be adjusted to an individual patient's foot size to prevent decubitus ulceration of the heel area of a patient; and individually cut to accommodate a particular foot.

And yet another object of this invention is to provide a heel suspending device to prevent ulceration on the heel area that has changable layers of support for improved hygiene.

And yet another object of this invention is to provide a light weight foot support that enhances dorsiflexion with minimal pressure from the support device itself, enhances layer rigidity, creates a buoyant effect, decreases ulceration in strap area and Achilles' tendon area, and allows for application of medicants to the foot area.

BRIEF DESCRIPTION OF THE DRAWINGS

FIG. 3 shows a side elevational view in cross section, with the supporting layers separated or exploded through line AA of FIG. 1.

FIG. 4 shows a perspective view of one embodiment showing the particular strap array useful to the present invention.

FIG. 5 shows a perspective view of the present invention with the straps disposed in an alternate mode of operation.

PREFERRED EMBODIMENT OF THE INVENTION

Figure 1:
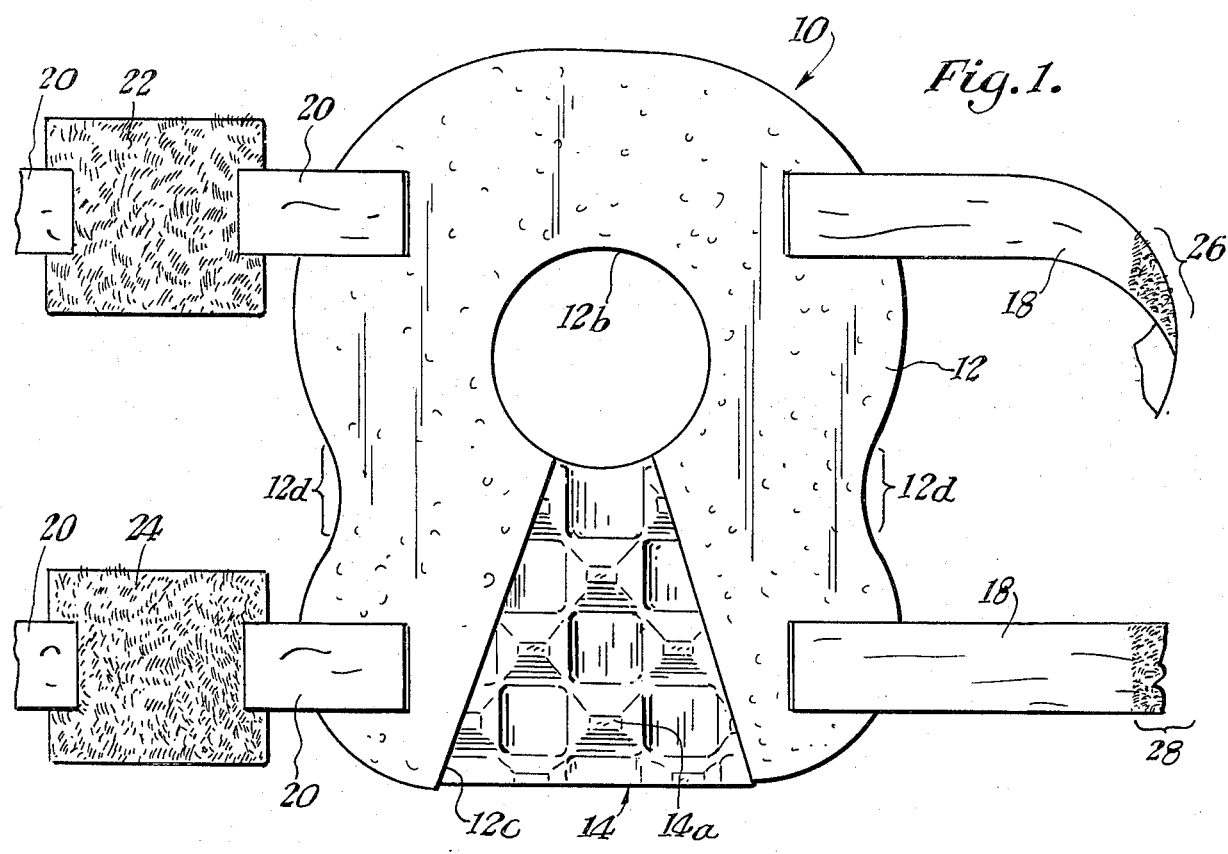
FIG. 1 shows a top plan view of the present invention including fragmentary views of the restraining straps.
Figure 2:
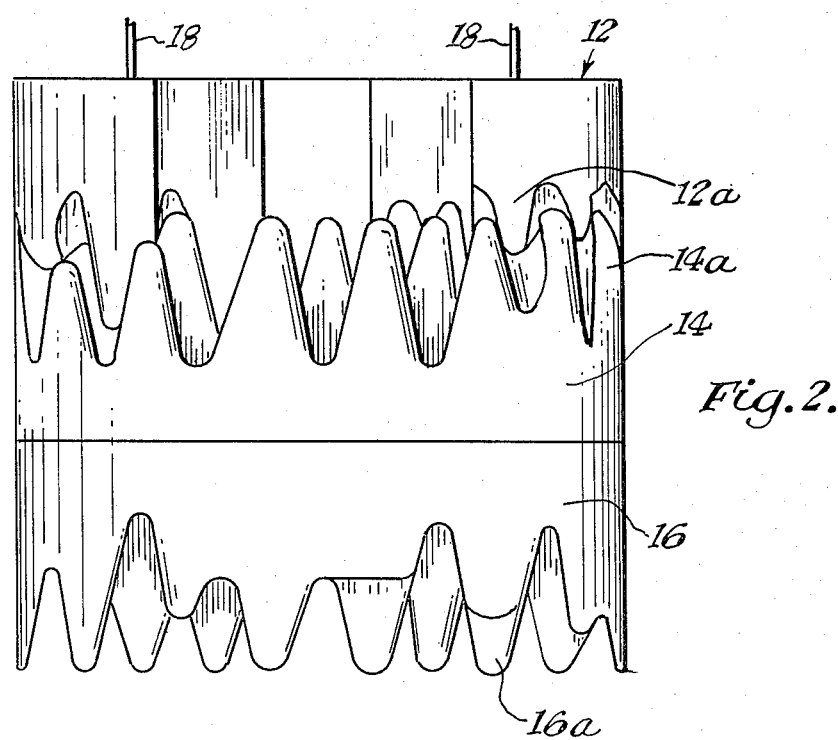
FIG. 2 shows a front elevational view of the device shown in FIG. 1.

Referring now to the drawings and specifically FIGS. 1 and 2, the present invention is shown generally at 10 comprised of three separate layers of foam 12, 14 and 16 held together in a stacked array by a pair of foot attaching straps 18 and 20. Each strap 18 and 20 is affixed to the three layers of foam 12, 14 and 16 through small apertures parallely aligned in succeeding layers such that strap 18 passes through the three layers across the bottom (not shown in FIG. 1) and back up through the layer. Strap 20 is likewise disposed.

The three layers of supporting foam 12, 14 and 16 have recessed side areas such as area 12d across the mid lateral sides which allow for comfortable support when the cushion is mounted on either side. Each layer 12, 14 and 16 has this recessed portion similar to that shown as 12b.

Additionally each foam layer 12, 14 and 16 includes a central somewhat circular aperture 12b, 14b and 16b which act to receive the heel.

Each of the foam layers 12, 14 and 16 include one surface of projecting members forming a series of undulations such as 12a, 14a and 16a. The surfaces being matched in a particular structural manner to enhance the overall operation of the device. Specifically, layers 12 and 14 are joined together across their undulated surfaces while layers 14 and 16 are formed along the flat portion of the foam with the resultant bottom layer 16 having its undulations downwardly disposed for engagement with the bed or other surface that the patient lying on. It is an important aspect of this invention that Applicant has determined that this arrangement produces the most desireable result in the form of support for the patient, stability of the cushion, preventing ulceration in the heel and Achilles' tendon area. This is clearly shown in FIG. 3 in an exploded view and in FIGS. 4 and 5 and 2.

The foot engaging straps which hold the cushion to the foot include two straps 18 and 20 each of which include a fabric fastener known under the trademark as "VELCRO" in areas such as 26 and 28. Looking specifically at FIGS. 4 and 5, it can be seen that the straps in accordance with the present invention can be arranged in two particular ways which allow for a change in the restraining straps to prevent ulceration along the leg or ankle portions of the patient. This allows for adjustments of pressure which affect the contact pressure of the cushion and the strap pressure. Straps further include a pair of sheep skin pads 22 having a fur portion on one side 22a that engages the upper part of the patients leg or ankle area, preventing direct strap contact. The strap members themselves however include the fabric fasteners 26 and 28 which allow perfect adjustment as to size and pressure since the fabric fasteners are located all the way along the straps. The resilient or furry separators 22 which separate the strap from the patients leg or ankle are themselves movable along the strap for proper overall adjustment. Thus it is another important feature of the present invention that the foot engaging strap which hold the cushion to the patients foot and leg area can be arranged in two different modes of operation to allow for changes in pressure which is very important in attachment of the cushion to the patient over a long period of time.

It is believed that the undulations on the bottom surface of the bottom layer which is pocketed decreases overall surface contact generating a patients sensation of lighter weight.

As shown in FIGS. 4 and 5 and specifically FIG. 1 it is noted that the top foam layer includes a trapazoidal or pie shaped section or opening 14c which allow the leg and ankle portion to be received and mounted and supported within the device.

Another advantage of the present invention is that should any one of the layers become soiled, a particular layer may be replaced without having to dispose of the entire device. It is also noted that each of the layers (other than the top layer) may be identical in shape and in convoluted surface, with the top layer being similar but having an additional pie shaped cut away portion.

To operate the device, the straps as shown in FIG. 4 would be separated to allow insertion of the leg and foot portions so that the heel is clearly supported freely in the central apertures formed in the leg. The straps are then adjusted and the fabric fasteners tightened to a desireable pressure. When desired instead of the criss-cross array of FIG. 4, straps may be disposed as in FIG. 5, in a parallel fashion.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A therapeutic support device to prevent or assist in the healing of the decubitus ulceration on the heel of the foot comprising:

a resilient body, said resilient body formed from a plurality of individual, resilient foam layers, each layer disposed in a stacked array, each of said layers having a substantially central aperture sized to receive the heel area of a foot with sufficient spacing around the heel area to that the heel area does not contact the surrounding surface formed from the aperture disposed within each layer, the layer apertures being stacked to form a single substantially central aperture in said resilient body, each of said layers having first, second and third and fourth strap receiving apertures, said first and second strap receiving apertures being disposed centrally on one side of said central aperture, and said third and fourth apertures being disposed essentially on the opposite side of said central aperture in each layer, each of said layers having a substantially flat surface and on the opposite side an undulated wavy surface formed from a plurality of pockets, said top layer having its undulated surface disposed downwardly, said top layer including a pie shaped passage from a peripheral edge to said central aperture, said second layer engaging said top layer having an undulated surface engaging the undulated surface of said top layer, and said bottom layer having its undulating surface disposed downwardly such that the flat surface of the second layer engages the flat surface of the bottom layer; and a first strap connected through said first and second strap apertures in each of said layers and a second strap disposed through said third and fourth apertures in each of said layers, said first and second straps including an adjustable connecting means whereby the ends of said first, second, third and fourth straps can be removably connected in either a parallel or criss-cross array to encircle the dorse part of the foot when the heel is disposed within the central aperture.

2. A protective cushion for the foot as in claim 1, including:

resilient furry pads adjustably connected to at least one of said straps, said pad surface portion being engageable with the skin area of the user when the strap is attached to the user in either mode of operation, whether parallel or criss-cross.

* * * * *